(12) United States Patent
Webster

(10) Patent No.: US 11,186,690 B2
(45) Date of Patent: Nov. 30, 2021

(54) NANOSTRUCTURED BACTERIA-RESISTANT POLYMER MATERIALS

(71) Applicant: Northeastern University, Boston, MA (US)

(72) Inventor: Thomas J. Webster, Barrington, RI (US)

(73) Assignee: Northeastern University, Boston, MA (US)

( * ) Notice: Subject to any disclaimer, the term of this patent is extended or adjusted under 35 U.S.C. 154(b) by 51 days.

(21) Appl. No.: 16/709,268

(22) Filed: Dec. 10, 2019

(65) Prior Publication Data

US 2020/0115513 A1    Apr. 16, 2020

Related U.S. Application Data

(62) Division of application No. 14/917,138, filed as application No. PCT/US2014/055427 on Sep. 12, 2014, now Pat. No. 10,501,589.

(Continued)

(51) Int. Cl.
*C08J 5/00* (2006.01)
*C08J 3/24* (2006.01)
(Continued)

(52) U.S. Cl.
CPC .............. *C08J 5/00* (2013.01); *A01N 25/08* (2013.01); *A61L 27/50* (2013.01); *A61L 29/06* (2013.01); *A61L 29/14* (2013.01); *A61L 31/10* (2013.01); *A61L 31/14* (2013.01); *B01J 3/006* (2013.01); *C08J 3/24* (2013.01); *A61L 2400/12* (2013.01); *A61L 2400/18* (2013.01);

*A61L 2420/02* (2013.01); *C08J 2323/06* (2013.01); *C08J 2323/12* (2013.01); *C08J 2325/06* (2013.01);
(Continued)

(58) Field of Classification Search
None
See application file for complete search history.

(56) References Cited

U.S. PATENT DOCUMENTS

| 4,001,432 A | 1/1977 | Green et al. |
| 4,696,842 A | 9/1987 | Doubt |

(Continued)

FOREIGN PATENT DOCUMENTS

| WO | 2011127463 A1 | 10/2011 | |
| WO | WO-2011127463 A1 * | 10/2011 | ............. B44C 1/227 |

(Continued)

OTHER PUBLICATIONS

Whang, K., et al., A novel method to fabricate bioabsorbable scaffolds, Polymer 36 (1995) pp. 837-842. (Year: 1995).*

(Continued)

*Primary Examiner* — Dominic Lazaro
(74) *Attorney, Agent, or Firm* — Verrill Dana, LLP

(57) ABSTRACT

Methods for creating nanostructured surface features on polymers and polymer composites involve application of low pressure during curing of solid polymer material from a solvent solution. The resulting nanoscale surface features significantly decrease bacterial growth on the surface. Polymer materials having the nanoscale structuring can be used in implantable medical devices to inhibit bacterial growth and infection.

20 Claims, 6 Drawing Sheets

Related U.S. Application Data

(60) Provisional application No. 61/877,063, filed on Sep. 12, 2013.

(51) Int. Cl.
| | |
|---|---|
| *B01J 3/00* | (2006.01) |
| *A61L 31/10* | (2006.01) |
| *A61L 29/06* | (2006.01) |
| *A01N 25/08* | (2006.01) |
| *A61L 31/14* | (2006.01) |
| *A61L 29/14* | (2006.01) |
| *A61L 27/50* | (2006.01) |

(52) U.S. Cl.
CPC ........ *C08J 2367/04* (2013.01); *C08J 2371/10* (2013.01); *C08J 2375/04* (2013.01); *C08J 2379/04* (2013.01)

(56) References Cited

U.S. PATENT DOCUMENTS

| | | |
|---|---|---|
| 7,622,127 B2 | 11/2009 | Haberstroh et al. |
| 7,838,074 B2 | 11/2010 | Brinkmann et al. |
| 7,846,466 B2 | 12/2010 | Shea et al. |
| 8,168,076 B2 | 5/2012 | Gavillet et al. |
| 8,192,765 B2 | 6/2012 | Sarangapani |
| 8,486,280 B2 | 7/2013 | Lee et al. |
| 8,518,963 B2 | 8/2013 | Ali et al. |
| 8,545,866 B2 | 10/2013 | Cotton et al. |
| 2013/0199539 A1 | 8/2013 | Webster |

FOREIGN PATENT DOCUMENTS

| | | |
|---|---|---|
| WO | 2013048785 A1 | 4/2013 |
| WO | 2013071316 A2 | 5/2013 |

OTHER PUBLICATIONS

Stout et al. Mechanisms of greater cardiomyocyte functions on conductive nanoengineered composites for cardiovascular application. Int J Nanomedicine. 2012; 7: 5653-5669.

Zhang et al. Decreased lung carcinoma cell density on select polymer nanometer surface features for lung replacement therapies. International Journal of Nanomedicine 2010:5 269-275.

Knetsch & Koole. New Strategies in the Development of Antimicrobial Coatings: The Example of Increasing Usage of Silver and Silver Nanoparticles. Polymers 2011, 3, 340-366.

Yao et al. Nanostructured polyurethane-poly-lactic-co-glycolic acid scaffolds increase bladder tissue regeneration: an in vivo study. International Journal of Nanomedicine 2013:8 3285-3296.

Thapa et al. Polymers with nano-dimensional surface features enhance bladder smooth muscle cell adhesion. J Biomed Mater Res A. Dec. 15, 2003;67(4):1374-83.

Thapa et al. Nano-structured polymers enhance bladder smooth muscle cell function. Biomaterials 24 (2003) 2915-2926.

\* cited by examiner

NANOSTRUCTURED BACTERIA-RESISTANT POLYMER MATERIALS

CROSS REFERENCE TO RELATED APPLICATIONS

This application claims the priority of U.S. Provisional Application No. 61/877,063, filed 12 Sep. 2013, and PCT Application No. PCT/US2014/055427, filed 12 Sep. 2014. This application is a divisional of U.S. national phase application Ser. No. 14/917,138, filed 7 Mar. 2016. Each of the aforementioned applications is hereby incorporated by reference.

BACKGROUND

Several techniques have been used to improve the cytocompatibility of polymer surfaces by chemical or physical techniques for tissue engineering applications. For example, polyurethane (PU) and poly-lactic co-glycolic acid (PLGA} surfaces can be nanostructured by etching a polymer surface with solutions of $HNO_3$ and NaOH, respectively. Thapa, A, et al., Biomaterials (2003) 24:2915-2926; and Thapa, A, et al., J. Biomed. Mater. Res. (2003) 67A:1374-1383. Nanostructuring of polymer surfaces can improve cell adhesion and proliferation. Additional methods of nanostructuring polymer surfaces include electron beam lithography, mechanical brushing (e.g., U.S. Pat. No. 7,838,074), nanopatterning the surface of a metal mold (e.g., U.S. Pat. No. 8,168,076), ion beam etching, reactive ion etching, plasma etching, and plasma assisted chemical vapor deposition (PACVD) (e.g., U.S. Pat. No. 8,486,280).

Medical devices that are surgically implanted are subject to bacterial growth and biofilm formation on their outer surfaces, which often results in serious infections and the need to surgically remove or replace the device. Previous efforts to inhibit the growth of bacteria on such surfaces include chemical modification of the polymer surface (e.g., U.S. Pat. No. 4,001,432), and the application of coatings containing antimicrobial materials such as silver (e.g., U.S. Pat. No. 8,192,765). However, such methods remain subject to variability, poor durability, and potential toxicity.

Thus, there remains a need to develop new methods of nanostructuring polymer surfaces used in implantable medical devices and developing surfaces that resist bacterial adhesion and biofilm formation.

SUMMARY OF THE INVENTION

The present invention provides methods for creating nanostructured surface features on polymers and polymer composites using low pressure (i.e., vacuum). The methods of the invention create nanostructured surface features on polymers and polymer composites using low pressure conditions. Specifically, by allowing polymers to cure (solidify) under low pressure, distinct polymer nano features can be created which significantly alter cellular functions (such as decreasing bacterial growth). This is because nanostructured surface features alter surface energetics to control initial protein adsorption events important for altering cellular functions. This technology can be used while a polymer is being extruded, cast-mold, or after production in which small amounts of a solvent are added to the polymer as long as pressure is being applied.

The invention allows the creation of nanoscale surface features on polymers using pressure during the solidification process. The resulting nanoscale surface can control cell functions, such as decreasing bacterial responses to an implant bearing the material on its surface, without the use of drugs such as antibiotics or other antimicrobial agents. The methods of the invention involve simple application of low pressure in a process that can be used during medical device production or after medical device function.

The invention can be used to decrease bacterial adhesion and colonization by altering nanoscale surface roughness alone, thereby avoiding pharmaceutical agents or other bioactive agents which may have side effects and can complicate regulatory approval. Methods of the invention for introducing bacteriostatic nanostructuring of polymer surfaces are simple and inexpensive, and involve a process that can be used during medical device production or following medical device production. The technology will significantly enhance the useful lifetime of an implanted medical device. Examples of implantable medical devices that can utilize the technology include catheters, endotracheal tubes, orthopedic implants, vascular stents, pacemaker leads, cartilage implants, and any implants that employ polymers or polymer composites on a surface and are subject to causing infection.

One aspect of the invention is a method of nanostructuring a surface of a polymer material. The method includes the steps of: (a) providing a solution containing a polymer material dissolved in an organic solvent; and (b) evaporating the solvent at low pressure, whereby the polymer material solidifies into a solid form containing the polymer material. The low pressure applied in step (b) is preferably in the range from about 0 to about 5 millibars (mbar), i.e., less than about 5 mbar, and more preferably about 2 mbar or less than about 2 mbar, or even about 1 mbar or less than about 1 mbar. As a result of the method, a surface of the polymer material becomes nanostructured. The surface roughness is on the nanoscale (i.e., having features ranging in size from about 1 nm to about 999 nm or less than 1000 nm), and in preferred embodiments the features have maximum dimensions characterized by a root mean square (RMS) size of about 100 nm or less, or between 0 nm and 100 nm, or about 50 nm or less, or between about 0 nm and 50 nm. The nanostructuring provides the useful function of inhibiting the adhesion of bacteria to the surface, including pathogenic bacteria that can cause infections as a result of implanting a medical device. Such bacteria include *Pseudomonas aeruginosa*, *Escherichia coli*, *Staphylococcus aureus*, and *Staphylococcus epidermidis*.

The method can be performed using any polymer that can be dissolved in a solvent. Preferred polymers include poly-lactic co-glycolic acid (PLGA), polyurethane, polycaprolactone, poly-ether-ether-ketone (PEEK), polyethylene, polypropylene, polypyrrole, and polystyrene, as well as mixtures (i.e., co-polymers) thereof and polymer composites containing these polymers or mixtures thereof. Any solvent or mixture of solvents can be used that is capable of dissolving the polymer and capable of removal by evaporation under low pressure conditions. Preferred solvents include chloroform, dimethyl formamide (DMF), acetone, chlorobenzene, cyclohexanone, cyclopentanone, dimethyl sulfoxide (DMSO), nitrobenzene, 1, 2-dichlorobenzene, diisopropyl ketone, dioxane, ethylene chloride, isophorone, toluene, and mesityl oxide.

Another aspect of the invention is another method of nanostructuring a surface of a polymer material. The method includes the steps of: (a) providing an article or device containing a polymer material surface and an organic solvent capable of dissolving the polymer material; (b) applying the solvent to the polymer material surface, whereby a portion of the polymer material surface dissolves in the solvent; and (c) evaporating the solvent at low pressure, whereby the dissolved polymer material solidifies into a solid form comprising the polymer material. As a result of performing the method, a surface of the polymer material becomes nanostructured.

Yet another aspect of the invention is yet another method of nanostructuring a surface of a polymer material. The method includes the steps of: (a) providing a solution containing a melt of a polymer material, the melt containing a solvent that is volatile at an extrusion temperature of the melt; (b) extruding the melt from an extrusion device to form an extruded article containing the polymer material; and (c) evaporating the solvent from the extruded article at low pressure. As a result of performing the method, a surface of the polymer material becomes nanostructured.

Still another aspect of the invention is a polymer material having nanostructure on at least a portion of its surface. The nanostructuring is produced by a method including any of the previously described methods.

Even another aspect of the invention is a polymer material having nanostructuring on at least a portion of a surface of the material. The nanostructured surface contains protruding surface features having an RMS height, width, and/or length of about 100 nm or less.

Another aspect of the invention is an article of manufacture or a device containing any of the previously described nanostructured polymer materials 34 at a surface of the article or device.

DETAILED DESCRIPTION OF THE INVENTION

Figure 1A:
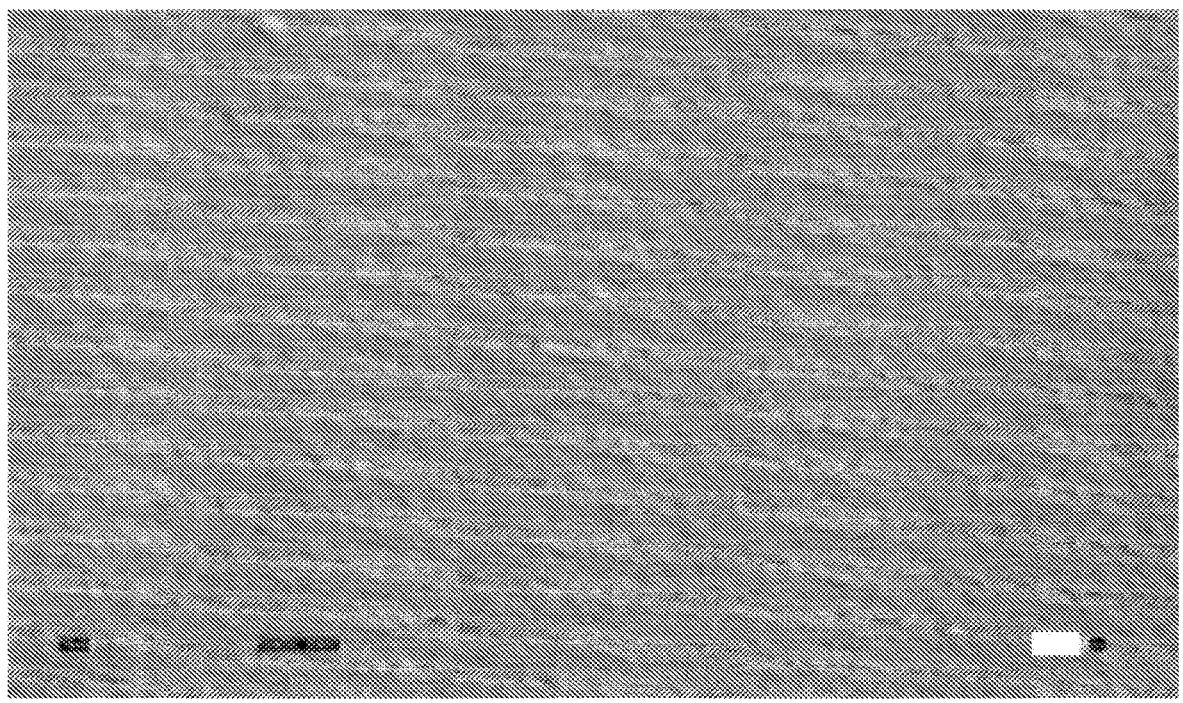
FIG. 1A shows nanoscale roughening of PLGA using low pressure (1 mbar) during solidification over 24 hours. The average feature size was: 25 nm diameter and 10 nm high.

The invention provides methods which utilize low pressure conditions to control solvent evaporation during solidification or curing of a polymer material, which results in nanostructuring of the material surface, or at least a portion of the material surface. When appropriately controlled, this curing process can create nanoscale surface features on polymers and polymer composites that are commonly used in implantable medical devices. During the application of the low pressure conditions (which can be adjusted to different polymers or polymer composites), the polymer slowly solidifies and forms surfaces with nanoscale surface features or roughness. These nanoscale surface features then in turn alter the surface energy of the material or a device made using the material. The change in surface energy in turn is believed to change the initial protein adsorption events that occur when the material is implanted into the body, thereby altering cellular responses to the implanted material or device. The result is a decrease in bacterial growth on the surface and an inhibition of biofilm formation on an implanted device containing the material. The technology can be used for any polymer and can be incorporated into procedures used during medical device fabrication, such as electro-spinning, extrusion, or molding. The methods of the present invention also can be used as a post-treatment following medical device fabrication.

In order to carry out a method according to the present invention, at least a portion of the polymer material is dissolved in a solvent. The concentration of dissolved polymer in the solvent can be any concentration consistent with the method of forming an article or device from the polymer. The polymer can be completely dissolved in the solvent, or the polymer can be only slightly or partially dissolved in the solvent, or in the case of a polymer melt, the solvent can be dissolved in the molten polymer. The solution or melt containing the polymer material and solvent can be placed into a mold or an extrusion device. A low-pressure condition is then applied to evaporate the solvent. As the solvent evaporates the polymer material begins to solidify into a solid form. During the final stages of solvent evaporation, nanostructuring of the solid form surface occurs as residual solvent leaves the surface of the forming polymer material. The result is a nanostructured polymer surface. The method can be carried out using practically any polymer material or copolymer material or even a composite material containing polymer material. A suitable solvent must be used which allows for the polymer material to be dissolved at least partially, and also allowing removal of the solvent by evaporation under suitable conditions of temperature and pressure.

Variations of the method also may be performed, wherein solvent, or a solvent-polymer solution, is applied to an already formed solid polymer material such that a portion of the polymer material is dissolved in the solvent, or such that a new layer of polymer material is laid down on the surface of the polymer material when the solvent evaporates. The solid form coated with solvent-polymer solution is then placed under appropriate vacuum conditions for evaporation of the remaining solvent. Yet another variation of the method can be performed wherein a polymer melt containing a small amount of solvent is placed into an extrusion device. For example, the polymer melt can contain 10% or less, 5% or less, 1% or less, or efen 0.1% or less of solvent by weight. The material is extruded from the device and then the extruded object is placed under low-pressure conditions under which the remaining solvent evaporates and creates nanostructure at the material surface. Alternatively, a freshly extruded solid object can be coated with solvent during its curing process, and placed into a vacuum chamber.

Structures formed at the surface of the polymer material can vary in the range from the nanoscale (from 1 to 999 nm) to the microscale (from 1 to 999 µm); however, structures in the nanoscale range are of interest in terms of their effects on surface energy and protein and cellular adsorption to the surface. Nanoscale surface structures can have various geometries, but generally take the form of approximately spherical or hemispherical structures having a diameter of about 100 nm or less, or 50 nm or less, or from 1 to 10 nm, or from 1 to 20 nm. The height of such structures may range, for example, from 1 to 100 nm, from 1 to 20 nm, from 1 to 10 nm, or from 1 to 5 nm. Nanoscale surface structures may take various forms on a given surface and may show a range of size and form distribution. For example, size distribution of nanoscale features may have distribution which can be described as having a root mean square (RMS) value from 1 to 100 nm, from 1 to 50 nm, from 1 to 20 nm, less than 100 nm, less than 50 nm, or less than 20 nm, for example. In some embodiments the RMS feature size may be 5 nm or less, or 10 nm or less. In certain embodiments the vertical height above the surface may be less than the lateral size of surface features. In general, surface features which have the ability to inhibit binding of bacterial cells to the surface are preferred.

The invention can be practiced over a range of low absolute pressures, i.e., vacuum pressures well below one atmospheric pressure, such as pressures of 20 mbar or less, 10 mbar or less, 5 mbar or less, 2 mbar or less, about 1 mbar, or less than 1 mbar. Suitable pressures can be found by testing different solvent temperature and viscosity conditions, and may need to be adjusted for different polymers. Factors that may be important for adjusting the formation of nanostructures while carrying out a method according to the invention include temperature, rate of change of temperature, the viscosity of the solvent-polymer solution, concentration of polymer in solution, time of evaporation, pressure during evaporation, and pressure gradients. For example, a suitable range of temperature during the evaporation process is from 0 to 70° C., a suitable rate of change of temperature is from 0 to 20° C. per minute, a suitable range of viscosity is from $10^{-2}$ to $10^{12}$ poise, a suitable concentration of the polymer in organic solvent solution is from 0 to 99% by weight, a suitable time of evaporation is up to one week, suitable pressure gradients include 0-10 mbar, and a suitable rate of pressure change is from 0 to 5 mbar per minute.

Any type of polymer, copolymer, or polymer composite material can be used with a method of the invention. Preferred polymers include PEEK, PU, PE, and PLGA. Composite materials can include inclusions such as carbon fiber, nanotubes (e.g., single-walled or multi-walled carbon nanotubes), nanoparticles, crystals, or other filler or reinforcing materials. Such materials can be added, for example, to the solvent-polymer solution.

Without intending to limit the invention to any particular mechanism, it is believed that the effect of nanoscale surface features on bacteria is mediated through alteration of the surface energy of the polymer material, which affects the adsorption of protein and bacterial cells to the surface. The size of the nanoscale features may be relevant in differentiating between bacterial cells, which should be excluded, and mammalian cells which need to adhere to the device for its effective use. Methods of the invention can be adjusted to provide desired nanoscale features on a polymer surface, and the effect of such features on bacterial adsorption and colonization of the material can be tested using bacterial growth on the material in culture.

A variety of medical devices utilizing the nanostructured polymer materials can be implanted into the living body of a subject. The subject can be, for example, a human patient, a mammal, or another animal. The device can either be entirely fabricated out of polymer material, or the polymer material can be used to form a portion of the device such as a coating on the surface of the device, or to form an exposed substructure of the device. While the nanostructuring of the invention can be employed on any medical device, particularly medical devices that are implanted, the nanostructuring can be especially useful on devices that are subject to infection when implanted. Preferred devices for use with the nanostructuring of the invention include catheters, endotracheal tubes, orthopedic implants, vascular stents, heart valves, pacemaker leads, cartilage implants, and bone implants.

The invention also can be used in the production of other articles of manufacture, including hand-held consumer articles which are not intended for medical use, such as switches, knobs, buttons, writing implements, or touchscreens, particularly where there is a desire to prevent bacteria and/or protein from adsorbing to the surface of the article.

EXAMPLES

Example 1. Nanostructuring of a PLGA Polymer Surface

Figure 1B:
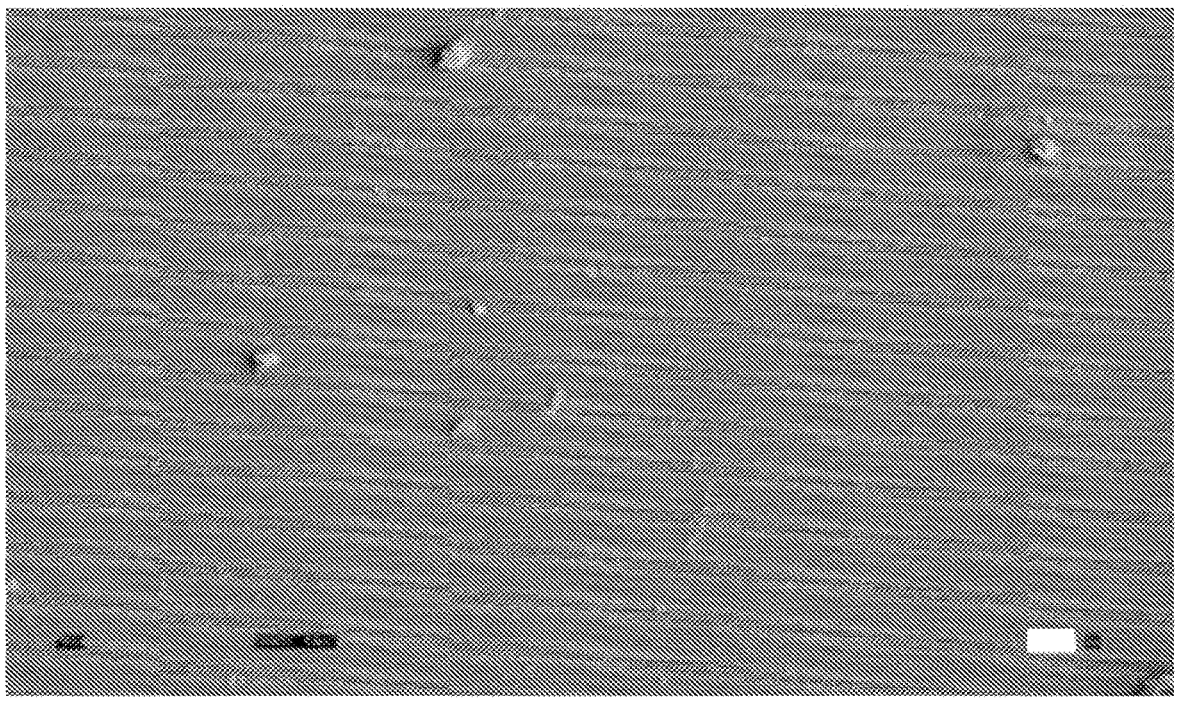
FIG. 1B shows lack of such nanoscale surface structure when solidification was performed at ambient conditions (1 bar). Scale bar=1 µm.

Poly-lactic-co-glycolic acid (50:50% PLA:PGA; Polysciences) was poured into a Petri dish after being dissolved in chloroform. The soluble PLGA was then placed in a pressure chamber to allow the polymer to solidify at two mbar absolute pressure and 26° C. for 48 hours. The low pressure condition was established and maintained by continuous operation of a vacuum pump. SEM images demonstrated a nanostructured surface for the PLGA allowed to solidify at low pressure (FIG. 1A), while images of the same PLGA-chloroform solution allowed to solidify under ambient conditions (1 bar absolute pressure) showed a smooth surface (FIG. 1B).

Example 2. Inhibition of Bacterial Growth on a Nanostructured PLGA Surface

A bacterial cell line of *Pseudomonas aeruginosa* (*P. aeruginosa*) was obtained in freeze-dried form from the American type culture collection (catalog number 27853; Manassas, Va., USA). The bacterial cells were propagated in 30 mg/mL tryptic soy broth (TSB) (catalog number 22092, Sigma-Aldrich, St. Louis, Mo., USA) for 24 hours in an incubator (37° C., humidified 5% carbon dioxide). When the second passage of bacteria reached its stationary phase, the second passage was frozen in one part TSB and one part 40% sterile glycerol. Before bacterial seating, a sterile 10 µL loop was used to withdraw the bacteria from the prepared frozen stock and streaked onto a TSB agar plate, and the TSB agar plate was incubated for 20 hours to form single bacterial colonies. The bacterial solution was diluted to a concentration of $10^7$ bacteria/mL, which was assessed by measuring the optical density of the bacterial solution using a standard curve correlating optical densities and bacterial concentrations. The optical densities were measured at 562 nm using a SpectraMax M5 plate reader (Molecular Devices, Sunnyvale, Calif.).

Bacteria ($10^5$ bacteria) were then seeded onto the samples of interest for 24 hours. At that time, bacteria were removed, diluted with a PBS solution, and were spread on agar plates where bacterial colonies were counted. Bacterial growth tests were conducted in triplicate and repeated three times. Data were collected and differences were assessed with the probability associated with a one-tailed Student's t-test.

Figure 2:
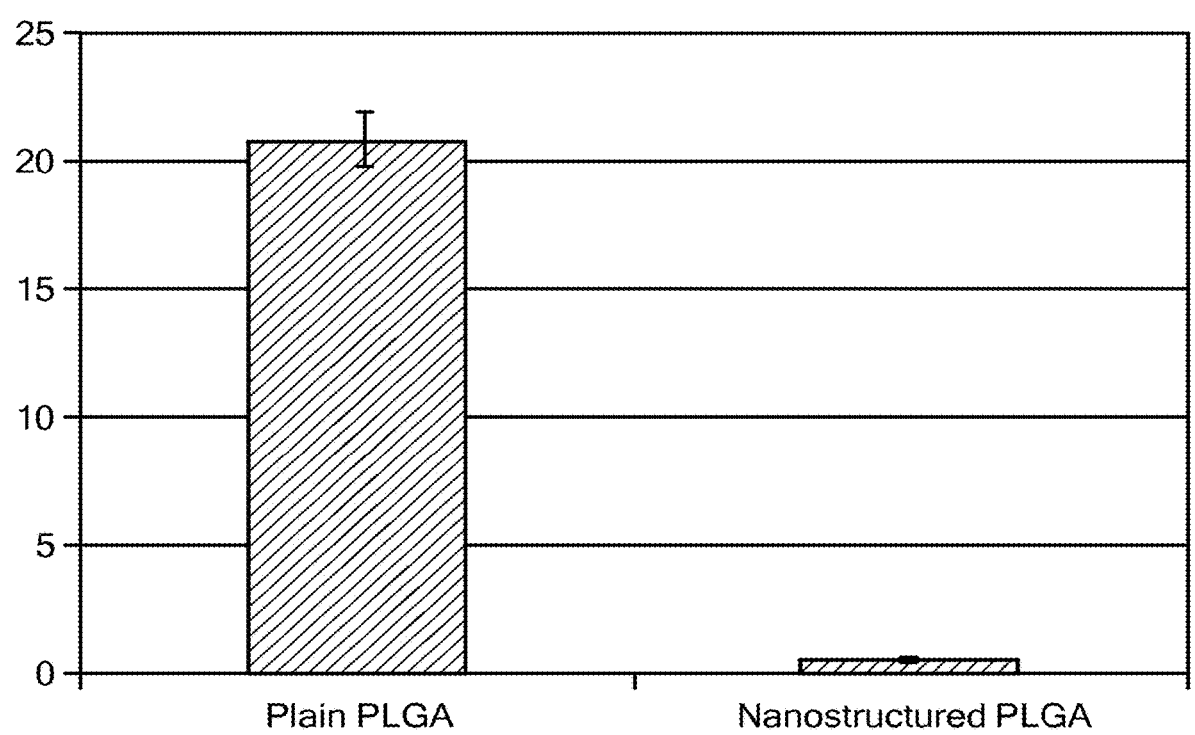
FIG. 2 shows decreased $P.$ $aeruginosa$ colony forming units on nanostructured PLGA. The y-axis is in units of $10^7$ colony forming units. The data shown are mean±SEM, n=3, *$p<0.01$ compared to plain (non-vacuum treated and unstructured) PLGA.

The results showed significantly fewer bacteria on the nanostructured PLGA compared to plain (untreated) PLGA (FIG. 2).

Example 3. Comparison of Nanostructuring of Different Polymer Materials

Nanostructuring was performed on several different polymer materials using a procedure similar to that described in Example 1. Each material showed nanostructuring after the solvent evaporation process was carried out at low pressure.

Figure 3A:
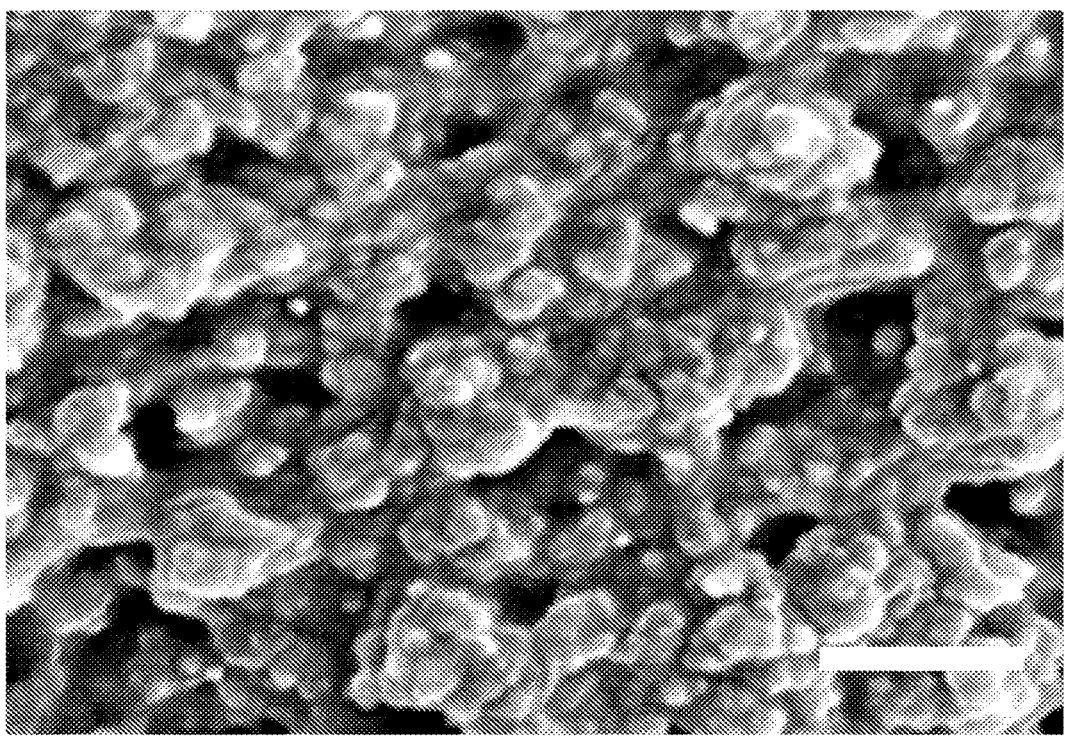
FIG. 3A shows nanoscale structuring of PEEK using low pressure (1 mbar) during solidification over 24 hours. The average feature size: was 45 nm diameter and 30 nm high.
Figure 3B:
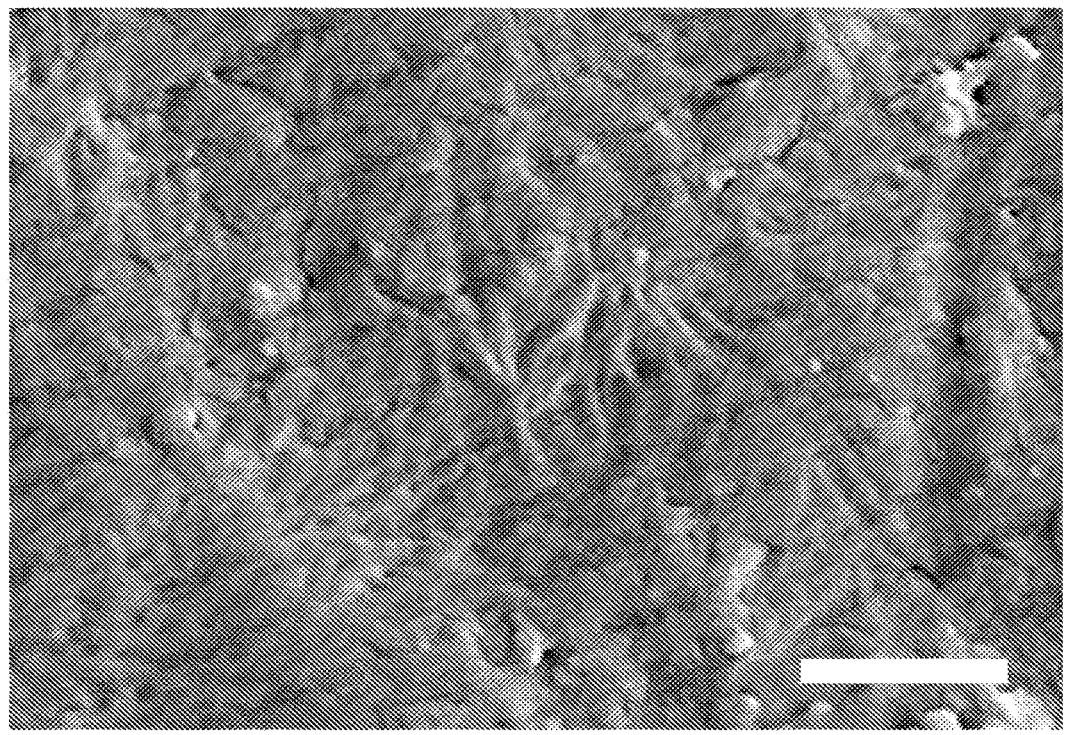
FIG. 3B shows surface structure when solidification was performed at ambient conditions (1 bar). Scale bar=500 nm.

Polyether ether ketone (PEEK, obtained from Invibio, Inc. was dissolved in dichloroethane at a concentration of 1 μg/mL and then the solvent was evaporated at 1 mbar pressure and 26° C. for 24 hours. FIG. 3A shows an SEM image of the surface structure after this process. The average surface feature size was 45 nm in diameter and 10 nm height. FIG. 3B shows a comparable image from a control PEEK surface produced by evaporation of the solvent at atmospheric pressure and 26° C. for 24 hours.

Figure 4A:
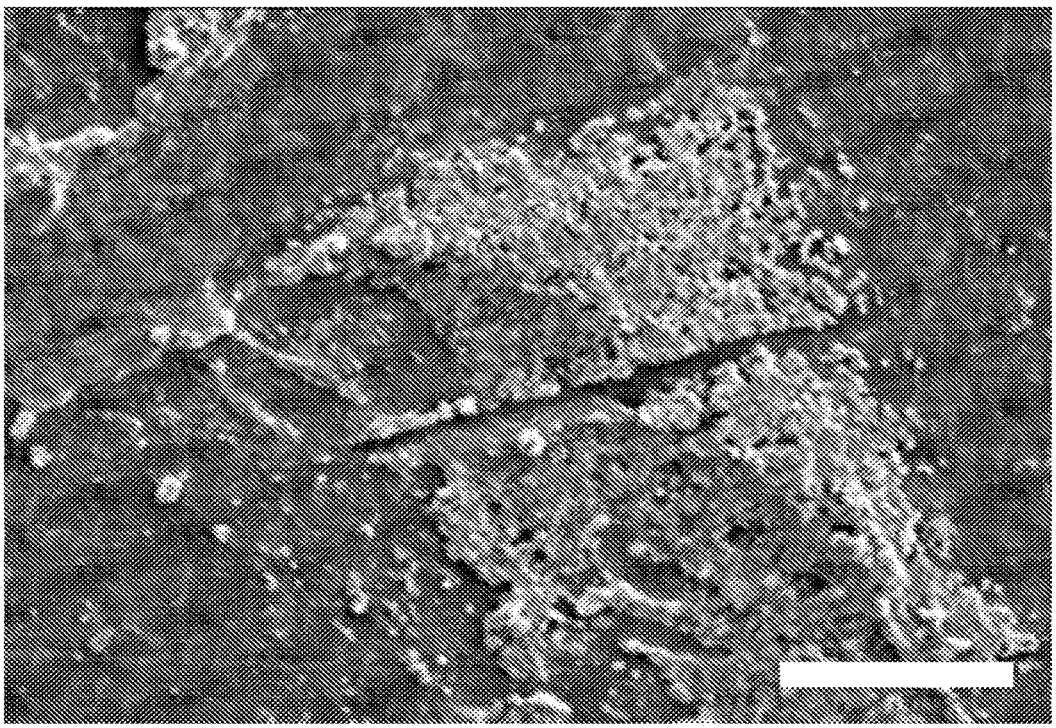
FIG. 4A shows nanoscale structuring of polyurethane using low pressure (0.5 mbar) during solidification over 48 hours. The average feature size: was 10 nm diameter and 5 nm high.
Figure 4B:
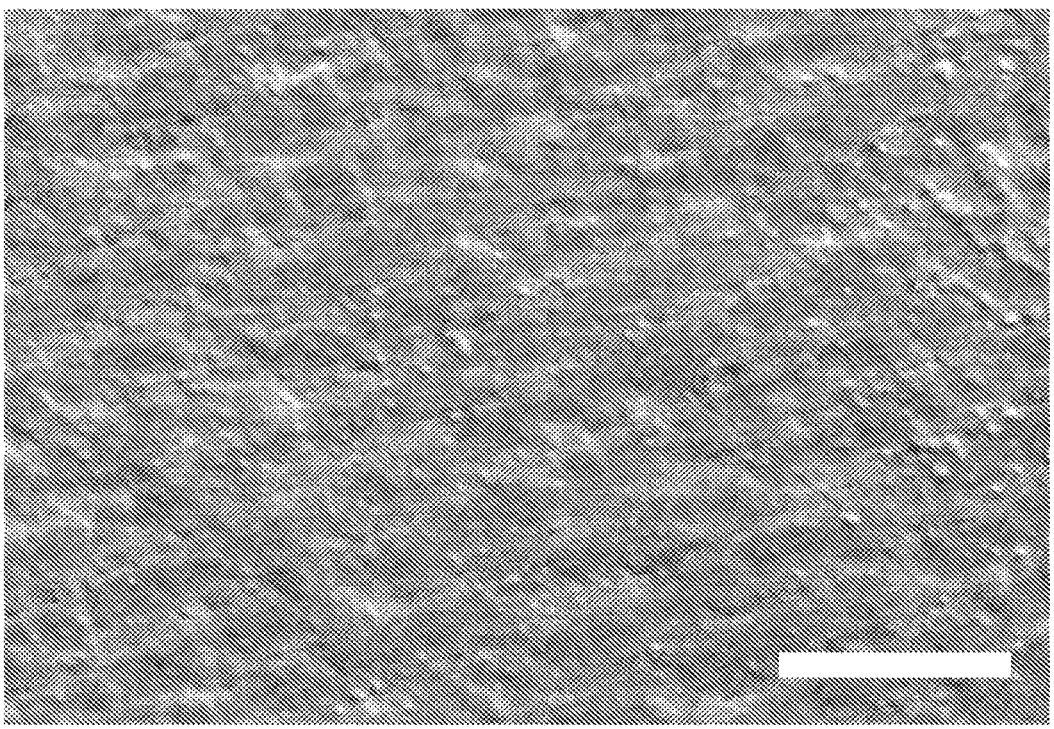
FIG. 4B shows surface structure when solidification was performed at ambient conditions (1 bar). Scale bar=1 micron.

Polyurethane (PU, obtained from Sigma-Aldrich) was dissolved in chloroform at a concentration of 10 μg/mL and then the solvent was evaporated at 0.5 mbar pressure and 26° C. for 48 hours. FIG. 4A shows an SEM image of the surface structure after this process. The average surface feature size was 10 nm in diameter and 5 nm height. FIG. 4B shows a comparable image from a control PU surface produced by evaporation of the solvent at atmospheric pressure and 26° C. for 48 hours.

Figure 5A:
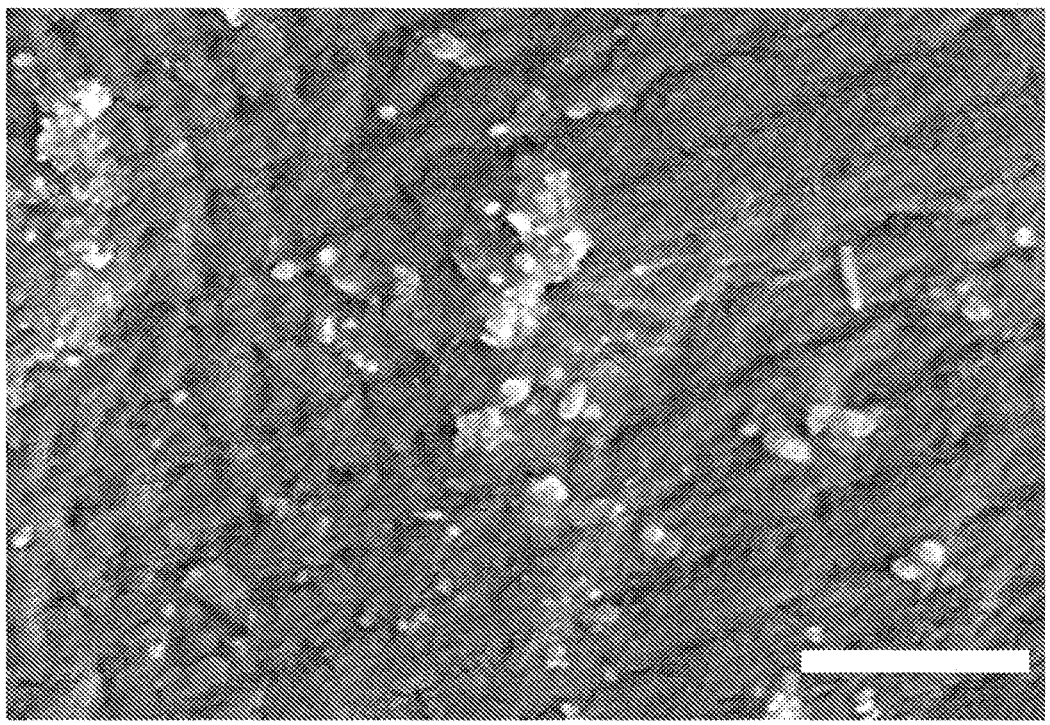
FIG. 5A shows nanoscale structuring of polyethylene using low pressure (1.5 mbar) during solidification over 12 hours. The average feature size: was 10 nm diameter and 5 nm high.
Figure 5B:
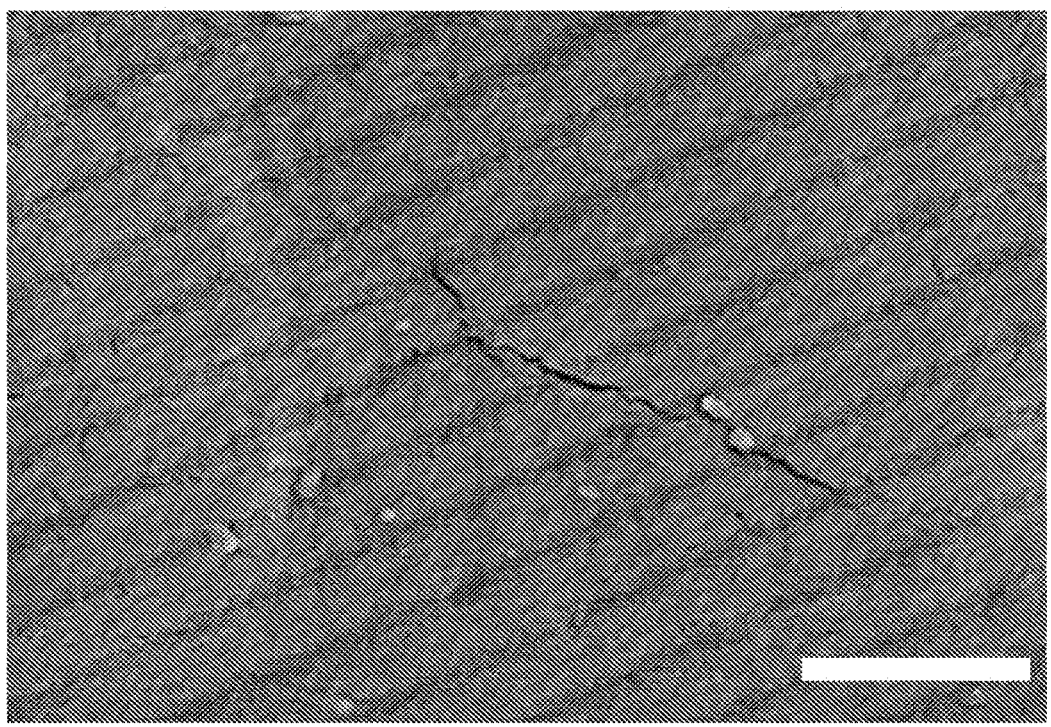
FIG. 5B shows surface structure when solidification was performed at ambient conditions (1 bar). Scale bar=1 micron.

Polyethylene (PE, Sigma-Aldrich) was dissolved in chloroform at a concentration of 5 μg/mL and then the solvent was evaporated at 1.5 mbar pressure and 26° C. for 12 hours. FIG. 5A shows an SEM image of the surface structure after this process. The average surface feature size was 10 nm in diameter and 5 nm height. FIG. 5B shows a comparable image from a control PE surface produced by evaporation of the solvent at atmospheric pressure and 26° C. for 12 hours.

Example 4. Inhibition of Bacterial Growth on a Nanostructured Polymer Surfaces

Figure 6:
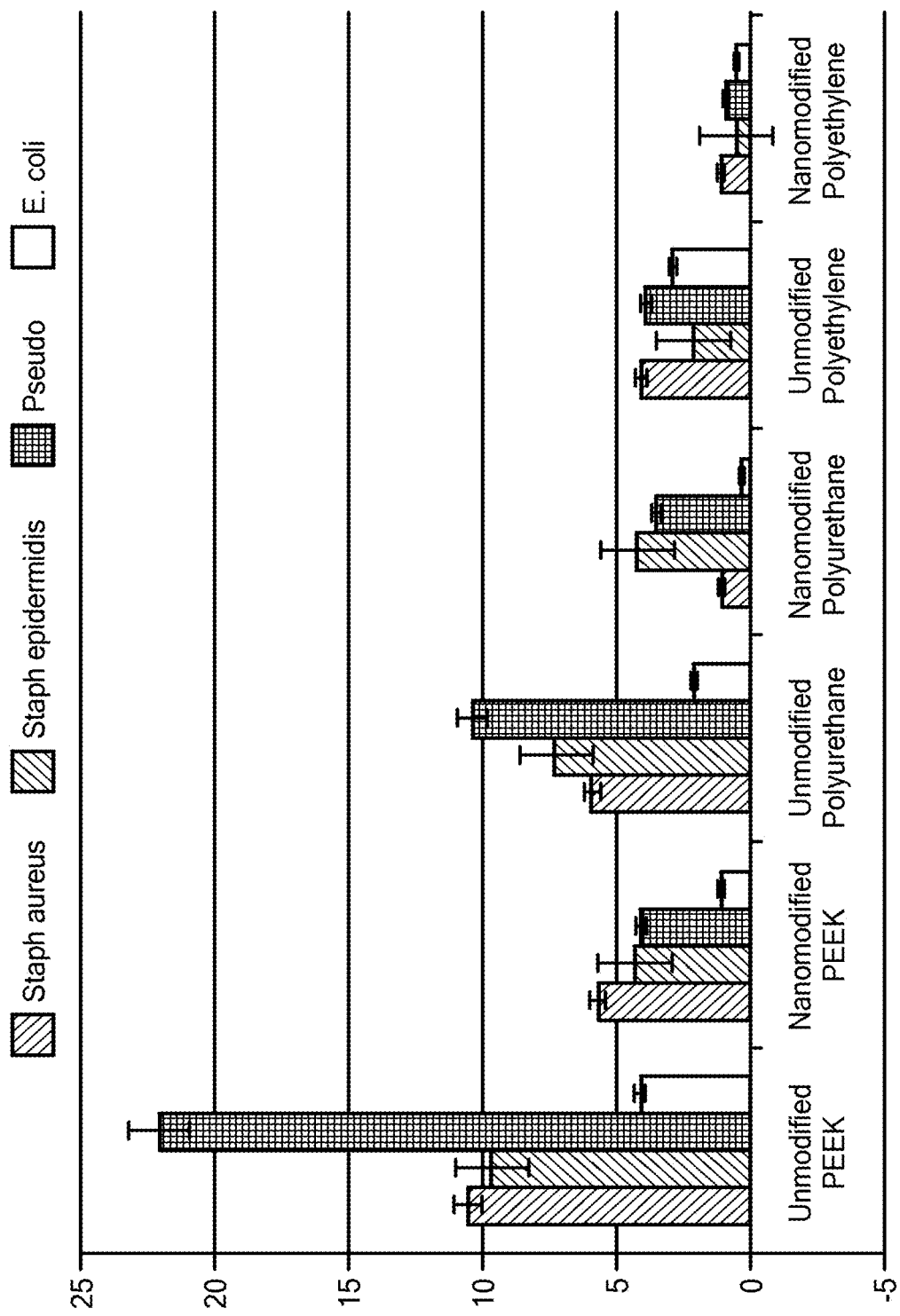
FIG. 6 shows the decrease in bacterial counts on nano-textured polymer surfaces. Data shown are mean+/−SEM, n=3. All values were significantly smaller on the nanomodified polymer surfaces compared to unmodified polymer surfaces at $p<0.01$. Time of culture was 24 hours. The y-axis shows units of $10^7$ colony forming units.

The nanostructured and unstructured polymer materials described in Example 3 were tested for the growth on their surfaces of four different bacterial species: *Staphylococcus aureus*, *Staphylococcus epidermidis*, *Pseudomonas aeroginosa*, and *Escherichia coli*. The procedure was as described in FIG. 2, and the results are shown in FIG. 6.

For each of the materials (PEEK, PU, and PE) the nanostructuring process ("nanomodified" in FIG. 6) significantly ($p<0.01$) reduced the growth of all tested bacterial species compared to the non-structured controls, As used herein, "consisting essentially of" does not exclude materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

The invention claimed is:

1. A polymer material comprising a nanostructured surface, the material produced by a method comprising the steps of:
    (a) providing a solution comprising a polymer material dissolved in an organic solvent; and
    (b) evaporating the solvent from the organic solvent solution at low pressure sufficient for nanostructuring a surface of the polymer material, whereby the polymer material solidifies into a solid form comprising the polymer material, wherein the surface of the polymer material is nanostructured, and wherein the nanostructured surface comprises protruding surface features that are spherical and/or hemispherical and have a diameter of about 100 nm or less.

2. The polymer material of claim 1, wherein the polymer material comprises a polymer selected from the group consisting of poly-lactic co-glycolic acid (PLGA), polyurethane, polycaprolactone, poly-ether-ether-ketone (PEEK), polyethylene, polypropylene, polypyrrole, and polystyrene.

3. The polymer material of claim 1, wherein the polymer material comprises two or more different polymers.

4. The polymer material of claim 1, wherein the polymer material is a composite material.

5. The polymer material of claim 1, wherein the organic solvent is selected from the group consisting of chloroform, dimethyl formamide (DMF), acetone, chlorobenzene, cyclohexanone, cyclopentanone, dimethyl sulfoxide (DMSO), nitrobenzene, 1, 2-dichlorobenzene, diisopropyl ketone, dioxane, ethylene chloride, isophorone, toluene, and mesityl oxide.

6. The polymer of claim 1, wherein the low pressure is in the range from about 0 to about 5 millibars.

7. The polymer of claim 6, wherein the low pressure is about 2 millibars.

8. The polymer material of claim 1, wherein the nanostructured surface is resistant to adhesion of bacteria.

9. The polymer material of claim 1, wherein the nanostructured surface is resistant to the formation of biofilms on said surface.

10. The polymer material of claim 9, wherein the nanostructured surface is resistant to formation of a biofilm on said surface by bacteria selected from the group consisting of *Pseudomonas aeruginosa*, *Escherichia coli*, *Staphylococcus aureus*, and *Staphylococcus epidermidis*.

11. The polymer material of claim 1, wherein the nanostructured surface has a root mean square (RMS) surface roughness of about 100 nm or less.

12. The polymer material of claim 1 that is essentially free of antimicrobial agents.

13. A polymer material comprising a nanostructured surface, the surface comprising protruding spherical and/or hemispherical surface features having an RMS of about 100 nm or less.

14. The polymer material of claim 13, wherein the protruding surface features have RMS diameter of about 50 nm or less.

15. The polymer material of claim 13, wherein the protruding surface features are essentially hemispherical in shape.

16. An article or device comprising the polymer material of claim 1 at a surface of the article or device.

17. The article or device of claim 16 that is implantable into a living subject.

18. The article or device of claim 17 that is selected from the group consisting of catheters, endotracheal tubes, orthopedic implants, vascular stents, heart valves, pacemaker leads, cartilage implants, and bone implants.

19. The article or device of claim 16 that is resistant to colonization of bacteria on said surface.

20. The article of claim 19 whose polymer surface is essentially free of antimicrobial agents.

* * * * *